United States Patent [19]

Tsutsumi et al.

[11] 3,984,462

[45] Oct. 5, 1976

[54] PROCESS FOR PRODUCING DODECANEDIOIC ACID DIMETHYL

[75] Inventors: Shigeru Tsutsumi, Hirakata; Yoshishige Kida, Kashihara, both of Japan

[73] Assignee: Okamura Oil Mill Limited, Osaka, Japan

[22] Filed: Dec. 20, 1974

[21] Appl. No.: 534,783

[30] Foreign Application Priority Data

Dec. 24, 1973 Japan................... 49-3593

[52] U.S. Cl.......................... 260/485 R; 260/610 R
[51] Int. Cl.$^2$........................................ C07C 67/42
[58] Field of Search................................ 260/485 R

[56] References Cited
UNITED STATES PATENTS

| | | | |
|---|---|---|---|
| 2,298,405 | 10/1942 | Milas............................... | 260/597 R |
| 2,601,224 | 6/1952 | Roedel............................ | 260/485 R |
| 2,811,551 | 10/1957 | Coffman.......................... | 260/485 R |
| 2,858,323 | 10/1958 | Smith.............................. | 260/485 R |
| 2,870,200 | 1/1959 | Kharasch........................ | 260/485 R |
| 3,590,080 | 10/1966 | Beesley........................... | 260/485 R |

OTHER PUBLICATIONS
Antonovskii, Chem. Abst., 65:6359d, (1966).
Brown, Chem. Abst., 50:24466, (1956).

Primary Examiner—Lorraine A. Weinberger
Assistant Examiner—Michael Shippen
Attorney, Agent, or Firm—Larson, Taylor and Hinds

[57] ABSTRACT

A process for producing dodecanedioic acid dimethyl ester comprising the steps of reacting cyclohexanone with methanol and hydrogen peroxide in the presence of an acid catalyst and water at a temperature below the boiling point of the methanol to produce methoxycyclohexyl peroxide, said methanol and hydrogen peroxide being used in an amount of about 15 to about 36 moles and in an amount of about 0.5 to about 1.5 moles per mole of the cyclohexanone respectively, dimerizing the resulting methoxycyclohexyl peroxide as it is contained in the reaction mixture in the presence of a ferrous salt and at least about 25 moles of methanol per mole of the starting cyclohexanone to produce dodecanedioic acid dimethyl ester, and separating the resulting dodecanedioic acid dimethyl ester from the reaction mixture.

3 Claims, No Drawings

PROCESS FOR PRODUCING DODECANEDIOIC ACID DIMETHYL

This invention relates to a process for producing dodecanedioic acid dimethyl ester and more particularly to an improved process for producing dodecanedioic acid dimethyl ester from cyclohexanone.

In the production of dodecanedioic acid dimethyl ester from cyclohexanone, it is known to produce dodecanedioic acid first and to esterify the acid in the usual manner. In the known process cyclohexanone is reacted with hydrogen peroxide in the presence of an acid catalyst and water to obtain cyclohexanone peroxide, which is then dimerized in the presence of a ferrous salt to obtain dodecanedioic acid. Since various complex side reactions occur in the course of the dimerization of cyclohexanone peroxide, this process gives the desired dodecanedioic acid in a very low yield, generally of about 25 to 30 mole %. In addition, cyclohexanone peroxide is explosive and therefore has the drawback of being troublesome to handle.

Thus the production of dodecanedioic acid dimethyl ester by the conventional process involves the drawback of low yields of dodecanedioic acid, which results in a similarly low yields of dodecanedioic acid dimethyl ester, the desired product.

An object of this invention is to provide a process capable of producing dodecanedioic acid dimethyl ester from cyclohexanone in a very high yield.

Another object of this invention is to provide a process for producing dodecanedioic acid dimethyl ester from cyclohexanone in which the hazard of explosion is greatly reduced.

Other objects of this invention will become apparent from the following description.

This invention provide a process for producing dodecanedioic acid dimethyl ester comprising the steps of reacting cyclohexanone with methanol and hydrogen peroxide in the presence of an acid catalyst and water at a temperature below the boiling point of the methanol to produce methoxycyclohexyl peroxide, said methanol and hydrogen peroxide being used in an amount of about 15 to about 36 moles and in an amount of about 0.5 to about 1.5 moles per mole of the cyclohexanone respectively, dimerizing the resulting methoxycyclohexyl peroxide as it is contained in the reaction mixture in the presence of a ferrous salt and at least about 25 moles of methanol per mole of the starting cyclohexanone to produce dodecanedioic acid dimethyl ester, and separating the dodecanedioic acid dimethyl ester from the reaction mixture.

We have conducted research on the process for producing dodecanedioic acid dimethyl ester and, in the course of the research, conceived an idea that dodecanedioic acid dimethyl ester might possibly be prepared if the reaction between cyclohexanone and hydrogen peroxide was conducted in the presence of methanol so as to obtain methoxycyclohexyl peroxide, followed by dimerization of the resulting peroxide, rather than the conventional process in which dodecanedioic acid prepared from cyclohexanone by way of cyclohexanone peroxide is esterified to obtain dodecanedioic acid dimethyl ester. We practiced this supposedly feasible process and found it possible to produce dodecanedioic acid dimethyl ester, although the yield of the desired product varies very widely depending on the amount of methanol used. Based on the novel finding, further research were conducted, which surprisingly revealed that dodecanedioic acid dimethyl ester, the desired product, can be obtained in a high yield of at least 70 mole %, when the reaction of cyclohexanone, hydrogen peroxide and methanol to produce methoxycyclohexyl peroxide is conducted using a large excessive amount, i.e., 15 to 36 moles of methanol per mole of cyclohexanone and the methoxycyclohexyl peroxide is dimerized in the presence of a ferrous salt and at least 25 moles of methanol per mole of cyclohexanone. It was also found to be essential to dimerize the resulting methoxycyclohexyl peroxide as it is contained in the reaction mixture obtained by the reaction to form methoxycyclohexyl peroxide from cyclohexanone (namely without separating the methoxycyclohexyl peroxide from the reaction mixture).

This invention has been accomplished based on these novel findings.

The reactions involved in the process of this invention are represented by the following equations:

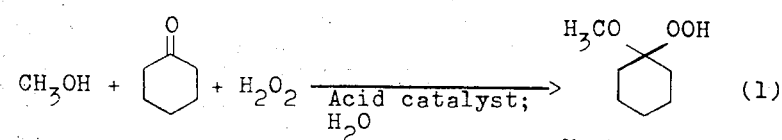

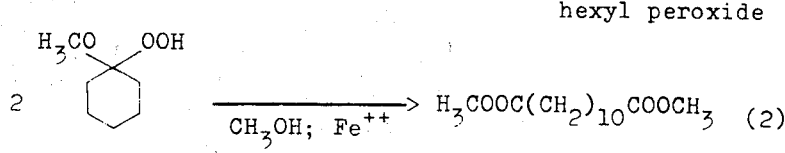

Supposedly the above reactions proceed as follows:

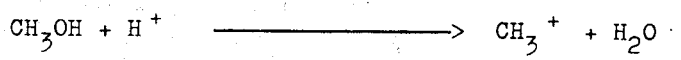

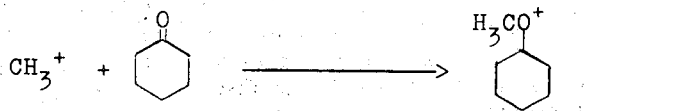

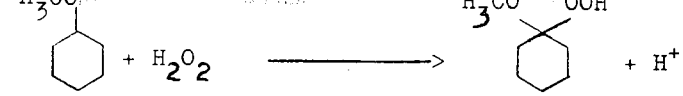

-continued

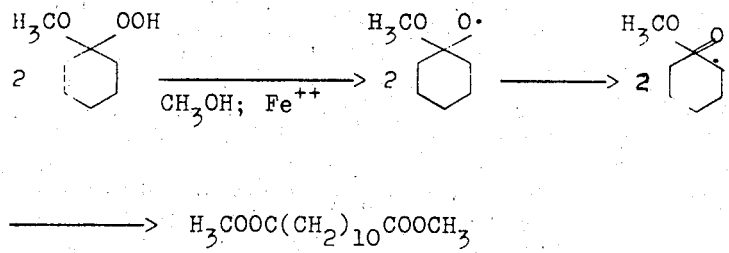

$$\longrightarrow H_3COOC(CH_2)_{10}COOCH_3$$

To practice the process of this invention, cyclohexanone, methanol and hydrogen peroxide are first reacted in the presence of acid catalyst and water.

It is especially critical to use about 15 to about 36 moles of methanol per mole of cyclohexanone. If the amount of methanol is less than about 15 moles, methoxycyclohexyl peroxide is obtained in a low yield and as a result dodecanedioic acid dimethyl ester will be obtained only in a very low yield. Preferably about 18 to about 30 moles of methanol is used per mole of cyclohexanone. The amount of hydrogen peroxide used in the present process is about 0.5 to about 1.5 moles, preferably about 0.7 to about 1.2 moles, per mole of cyclohexanone. Suitable for use as the acid catalyst are sulfuric acid, hydrochloric acid, nitric acid, phosphoric acid and like inorganic acids. The acid catalyst is used in an amount of at least 0.01 mole, preferably about 0.02 to 0.05 mole, per mole of cyclohexanone. The amount of water to be used is at least 2 moles, preferably 3 to 6 moles, per mole of cyclohexanone. It is preferred to use water mixed with hydrogen peroxide or methanol. The reaction can be conducted at a temperature below the boiling point of methanol, preferably at $-20°$ to $60°$ C. The reaction is allowed to proceed until cyclohexanone is almost wholly converted to methoxycyclohexyl peroxide.

The resulting methoxycyclohexyl peroxide is then subjected to a dimerization reaction without being separated from the reaction mixture. If methoxycyclohexyl peroxide is separated from the reaction mixture and then dimerized, the yield of dodecanedioic acid dimethyl ester is substantially reduced although the contributory cause has not been fully recognized.

The dimerization reaction is carried out in the presence of a ferrous salt and at least about 25 moles of methanol per mole of the starting cyclohexanone. The amount of methanol is critical and if it is less than about 25 moles, the yield of dodecanedioic acid dimethyl ester is seriously reduced. Preferable amount of methanol is in the range of 30 to 70 moles per mole of the starting cyclohexanone. The methanol present in the dimerization reaction system includes the unreacted methanol from the first step and methanol freshly added to the system. Therefore, if less than about 25 moles, per mole of the starting cyclohexanone, of methanol remains unreacted in the first step, fresh methanol should be added to the system so as to adjust the total methanol amount to at least about 25 moles per mole of the starting cyclohexanone. If the amount of unreacted methanol is more than about 25 moles per mole of the starting cyclohexanone, there is no need to add fresh methanol, although it can be added as desired.

Suitable for use as the ferrous salts are any of various known ferrous salts such as, for example, ferrous sulfate, ammonium ferrous sulfate, ferrous chloride, etc. The ferrous salt is used in a catalytic amount, preferably 0.5 to 5 moles per mole of the starting cyclohexanone, the most preferable amount being in the range of 0.7 to 2 moles per mole of the starting cyclohexanone.

The reaction mixture containing methoxycyclohexyl peroxide, ferrous salt and methanol can be mixed together in any desired order. However, it is preferable to mix methanol and ferrous salt and then to add the reaction mixture to the resulting mixture dropwise.

The dimerization reaction is conducted in air or preferably in inert gas atmosphere at a temperature of about $-20°$ to $60°C$, preferably about $5°$ to $15°C$.

The dodecanedioic acid dimethyl ester thus obtained can be easily separated from the resulting reaction mixture. For example, the reaction mixture is distilled to recover methanol and the residue is left to stand. The residue separates into two layers: an upper layer of dodecanedioic acid dimethyl and a lower layer of ferric sulfate solution. The dodecanedioic acid dimethyl ester layer is collected, and then washed with water and dried to obtain dodecanedioic acid dimethyl.

The process of the present invention can be carried out without any hazard of explosion since the intermediate, methoxycyclohexyl peroxide is far more stable as compared with cyclohexanone peroxide which is used as an intermediate in the conventional method.

For a better understanding of the invention examples are given below.

EXAMPLE 1

Into a reactor equipped with a stirrer is placed 3,200 g (100 moles) of methanol. While keeping the methanol at 5°C, 490 g (5 moles) of cyclohexanone and 20 g (about 0.2 mole) of concentrated sulfuric acid are added thereto, followed by stirring. Subsequently while maintaining the mixture at the same temperature, 580 g of 35% aqueous solution of hydrogen peroxide (6.0 moles of hydrogen peroxide is contained) is slowly added to the mixture. After the addition, the resulting mixture is further stirred for 10 minutes to complete the reaction to form methoxycyclohexyl peroxide.

In another reactor with its interior air replaced by nitrogen gas, 1760 g (55 moles) of methanol and 2,000 g (7.2 moles) of ferrous sulfate are mixed together. The reaction mixture obtained, above and containing methoxycyclohexyl peroxide is slowly added to the latter mixture maintained at 10°C, followed by stirring. Consequently the temperature of the contents of the reactor rises to 42°C, whereupon the reaction is completed. Through distillation of the reaction product obtained, about 4710 g of methanol is recovered, and 3380 g of the residue is left to stand. The residue separates into two layers: an upper layer of dodecanedioic acid dimethyl ester and a low layer of ferric sulfate solution. The dodecanedioic acid dimethyl ester layer is collected and washed with water to obtain 459 g of crude dodecanedioic acid dimethyl ester having an acid value of 6.1 and a saponification value of 426. When analyzed by gas chromatography, the product is found to contain 90.5 wt.% of dodecanedioic acid dimethyl ester and 9.5 wt.% of hydroxycaproic acid methyl. Based on cyclohexanone, the yield of dodecanedioic acid dimethyl ester is 70 mole %.

EXAMPLE 2

The same procedures as in Example 1 are followed except that the amount of methanol used in the reaction for preparing methoxycyclohexyl peroxide and the amount of methanol used in the reaction to produce dodecanedioic acid dimethyl ester are changed to the specified amounts listed in Table 1 below. The results are also given in Table 1.

Table 1

| | Amount of methanol | | | | |
|---|---|---|---|---|---|
| In the first step*[1] | | | | | |
| (g) | 1600 | 2240 | 2560 | 4800 | 5600 |
| (mole) | 50 | 70 | 80 | 150 | 175 |
| (mole per mole of cyclohexanone) | 10 | 14 | 16 | 30 | 35 |
| In the second step*[2] | | | | | |
| (g) | 4000 | 3360 | 3040 | 800 | 0 |
| (mole) | 125 | 105 | 95 | 25 | 0 |
| (total mole per mole of cyclohexanone) | 30 | 30 | 30 | 30 | 30 |
| Yield of dodecanedioic acid dimethyl ester (mole %) | 2.5 | 30.1 | 72.3 | 73.0 | 73.2 |

(Note)
*[1]Step of preparation of methoxycyclohexyl peroxide.
*[2]Step of preparation of dodecanedioic acid dimethyl ester.

EXAMPLE 3

The same procedures as in Example 1 are followed except that the amount of methanol used in the reaction to produce dodecanedioic acid dimethyl ester is changed to the specified amount listed in Table 2 below.

Table 2

| | Amount of methanol | | | | |
|---|---|---|---|---|---|
| In the second step | | | | | |
| (g) | 160 | 256 | 384 | 1120 | 1760 |
| (mole) | 5 | 8 | 12 | 35 | 55 |
| (total mole per mole of cyclohexanone) | 20 | 23 | 27 | 50 | 70 |
| Yield of dodecanedioic acid dimethyl ester (mole %) | 29.3 | 31.2 | 70.3 | 72.6 | 73.1 |

COMPARISON EXAMPLE

The same procedures as in Example 3 are followed except that in place of methanol used in the reaction to produce dodecanedioic acid dimethyl ester, acetone is used in the specified amount listed in Table 3. The results are also given in Table 3.

Table 3

| | Amount of acetone | | |
|---|---|---|---|
| In the second step | | | |
| (g) | 290 | 696 | 2030 |
| (mole) | 5 | 12 | 35 |
| Yield of dodecanedioic acid dimethyl ester (mole %) | 50.5 | 51.3 | 52.0 |

What we claim is:

1. A process for producing dodecanedioic acid dimethyl ester comprising the steps of reacting cyclohexanone with methanol and hydrogen peroxide in the presence of an acid catalyst and water at a temperature below the boiling point of the methanol to produce methoxycyclohexyl peroxide, said methanol and hydrogen peroxide being used in an amount of about 15 to about 36 moles and in an amount of about 0.5 to about 1.5 moles per mole of the cyclohexanone respectively, dimerizing the resulting methoxycyclohexyl peroxide as it is contained in the reaction mixture in the presence of a ferrous salt and at least about 25 moles of methanol per mole of the starting cyclohexanone to produce dodecanedioic acid dimethyl, and separating the resulting dodecanedioic acid dimethyl ester from the reaction mixture.

2. The process for producing dodecanedioic acid dimethyl ester according to claim 1, in which said methanol in the first step to produce methoxycyclohexyl peroxide is used in an amount of about 18 to about 30 moles per mole of cyclohexanone.

3. The process for producing dodecanedioic acid dimethyl ester according to claim 1, in which said methanol in the second step to produce dodecanedioic acid dimethyl ester is used in an amount of about 30 to about 70 moles per mole of cyclohexanone.

* * * * *